US007341718B2

(12) United States Patent
Millecamps-Navarro et al.

(10) Patent No.: US 7,341,718 B2
(45) Date of Patent: Mar. 11, 2008

(54) NEURONAL GENE TRANSFER OF ADENOVIRUS AND HERPES VIRUS VECTORS

(75) Inventors: Stéphanie Millecamps-Navarro, Paris (FR); Martine Barkats, Ivry sur Seine (FR); Jacques Mallet, Paris (FR)

(73) Assignee: Centre National de la Recherche Scientifique, Paris Cedex (FR)

( * ) Notice: Subject to any disclaimer, the term of this patent is extended or adjusted under 35 U.S.C. 154(b) by 66 days.

(21) Appl. No.: 10/476,076

(22) PCT Filed: May 15, 2002

(86) PCT No.: PCT/EP02/05354

§ 371 (c)(1),
(2), (4) Date: Feb. 24, 2004

(87) PCT Pub. No.: WO02/094308

PCT Pub. Date: Nov. 28, 2002

(65) Prior Publication Data

US 2004/0131593 A1   Jul. 8, 2004

(30) Foreign Application Priority Data

May 22, 2001 (EP) ................................. 01401342

(51) Int. Cl.
*A61K 48/00* (2006.01)
*C12N 15/861* (2006.01)
*C12N 15/869* (2006.01)

(52) U.S. Cl. ...................... 424/93.2; 424/93.1; 514/44; 435/320.1

(58) Field of Classification Search ...................... None
See application file for complete search history.

(56) References Cited

FOREIGN PATENT DOCUMENTS

| EP | 0 845 267 | 6/1998 |
|---|---|---|
| WO | WO 92/03155 | 3/1992 |
| WO | WO 92/05254 | 4/1992 |
| WO | WO 97/34567 | 9/1997 |
| WO | WO 00/24359 | 5/2000 |
| WO | WO 01/26736 | 4/2001 |

OTHER PUBLICATIONS

Kemplay et al., "Effects of acrylamide and botulinum toxin on horseradish peroxidase labelling of trigeminal motor neurons in the rat," J. Anat. 137(3): 477-482, 1983.*
Montecucco et al., "Structure and function of tetanus and botulinum neurotoxins," Quarterly Rev. Biophys. 28(4): 423-472, 1995.*
Perrelet et al., "IAP family proteins delay motorneuron cell death in vivo," Eur. J. Neurosci. 12(6): 2059-2067, Jun. 2000.*
Piehl et al., "Regulatory effects of trophic factors on expression and distribution of CGRP and GAP-43 in rat motoneurons," J. Neurosci. Res. 51: 1-14, 1998.*
Ye et al., "The herpes simplex virus 1 UL34 protein interacts with a cytoplasmic dynein intermediate chain and targets nuclear membrane," J. Virol. 74(3): 1355-1363, Feb. 2000.*
Chamberlin et al., "Recombinant adeno-associated virus vecotr: use for transgene expression and anterograde tract tracing in the CNS," Brain Res. 793 : 169-175, 1998.*
Mazarakis et al., "Rabies virus glycoprotein pseudotyping of lentiviral vectors enables retrograde axonal transport and access to the nervous system after peripheral delivery," Hum. Molec. Genet. 10(19): 2109-2121, Sep. 2001.*
Wang et al., "Transgene expression in the brain stem effected by intramuscular injection of polyethyleneimine/DNA complexes," Mol. Ther. 3: 658-664, May 2001.*
Bisby et al., "GAP-43 mRNA in mouse motoneurons undergoing axonal sprouting in response to muscle paralysis or partiel denervation," Eur. J. Neurosci. 8(6): 1240-1246, 1996.*
Bonner et al., "Botulinum A toxin stimulates neurite branching in nerve-muscle cocultures," Dev. Brain Res. 79: 39-46, 1994.*
Gurney et al., "Induction of motor neuron sprouting in vivo by ciliary neurotrophic factor and basic fibroblast growth factor," J. Neurosci. 12(8): 3241-3247, 1992.*
Stedman's Medical Dictionary 27th edition, definitions of analogous and analog, in PDR Electronic Library at www.thomsonhc/pdel/librarian/, accessed by PTO Sep. 25, 2006.*
Goebel et al, "Botulinum-Toxin A in the therapy of headache disorders and pericranial pain syndromes", Biosciences Information Service & Nervenarzt, vol. 72, No. 4, Apr. 2001, pp. 261-174, Abract only.
Eberhardt et al, "Combined neurorestorative and neuroprotective effects against MPTP toxicity by adenoviral delivery of both GDNF and XIAP into the mouse striatum", Biosciences Information Service & Society for Neuroscience Abstracts, vol. 26, No. 1-2, 2000, pp. Abstract No. -666.10.

(Continued)

*Primary Examiner*—Scott D. Priebe
(74) *Attorney, Agent, or Firm*—Nixon & Vanderhye P.C.

(57) ABSTRACT

The present invention is related to compositions and methods for the delivery of nucleic acids to neurons in a mammal, and uses thereof. The present invention specifically discloses the use of compounds that cause synaptic nerve sprouting to increase neuron retrograde transport of a vector or a product (a polypeptide or a nucleic acid for example) in a mammal. The invention is also based on the use of a compound that interacts with synaptosomal associated proteins to increase neuron retrograde transport of a vector or a product such as one cited above in a mammal. The invention also relates to a product comprising a viral vector comprising a transgene and a compound that causes synaptic nerve sprouting, for sequential use for delivering said transgene to neurons by retrograde transport and its uses for the preparation of a composition used as a treatment in several neurological disorders. The methods and compositions of this invention can be used to deliver various transgenes, such as markers, vaccines, therapeutic genes etc., and are suitable for experimental, therapeutic or various other applications.

13 Claims, 3 Drawing Sheets

OTHER PUBLICATIONS

Figure 2:
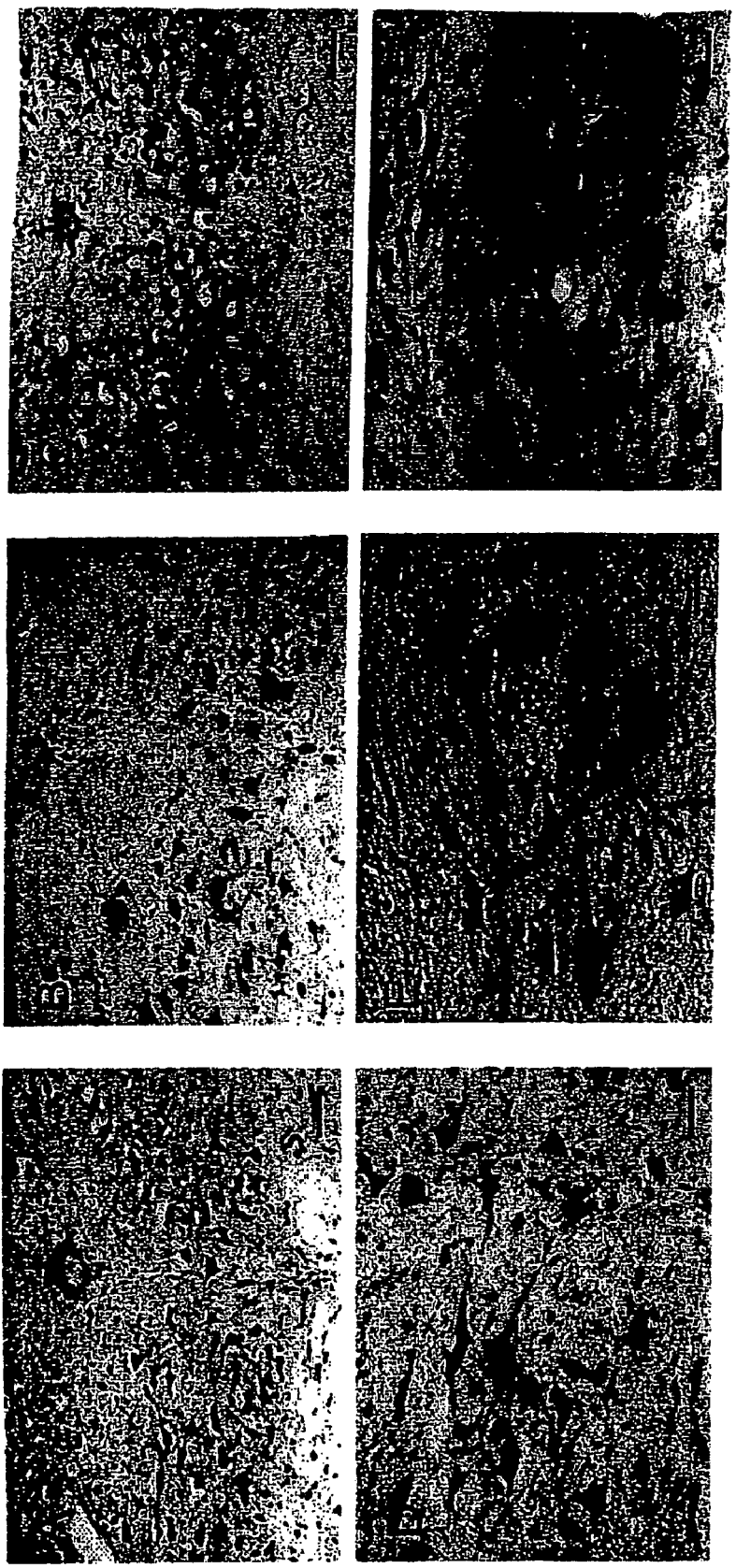

Eberhardt et al, "Protection by synergistic effects of adenovirus-mediated X-chromosome-linked inhibitor of apoptosis and glial cell line-derived neurotrophic factor gene transfer in the 1-methyl-4-phenyl-1,2,3,6-tetrahydropyridine model of Parkinson's disease", Biosiences Information Service & Journal of Neuroscience, vol. 20, No. 24, Dec. 15, 2000, pp. 9126-9134, Abstract only.

Ghadge et al, "CNS gene delivery by replication-defective adenoviruses", Biosciences Information Service & Gene Therapy, vol. 2, No. 2, 1995, pp. 132-137, Abstract only.

Finiels et al, "Specific and efficient potentialities for the treatment of motor retrieved from STN", US National Library of Medicine & Neuroreport, Dec. 29, 1995, 7 (1) 373-8, Abstract only.

White et al, "Repeated stimuli for axonal growth causes motoneuron death in adult rats: The effect of botulinum toxin followed by partial denervation", Biosciences Information Service & Neuroscience, vol. 95, No. 4, Dec. 30, 2000, pp. 1101-1109, Abstract only.

Bisby et al, "GAP-43 mRNA in mouse motoneurons undergoing axonal sprouting in response to muscle paralysis or partial denervation", Biosciences Information Service & European Journal of Neuroscience, vol. 8, No. 6, 1996, pp. 1240-1248, Abstract only.

Tian, "Uptake and retrograde axonal transport of horseradish peroxidase injected into botulinum toxin poisoned muscle in rats", Biosciences Information Service & ACTA Pharamacologica SINICA, vol. 3, No. 2, 1982, pp. 94-96, Abstract only.

Millecamps et al, "Synaptic sprouting increases the uptake capacities of motoneurons in amyotrophic lateral sclerosis mice", Proceedings of the National Academy of Sciences of the United States, vol. 98, No. 3, Jun. 19, 2001, pp. 7582-7587.

Millecamps et al, "Synaptic sprouting increases motoneuronal gene transfer using retrograde transport of adenoviral vectors", Biosciences Information Services & Society for Neuroscience Abstracts, vol. 27, No. 1, 2001, pp. 294.

Millecamps et al, "Adenoviral Retrograde Gene Transfer in Motoneurons is Greatly Enhanced by Prior Intramuscular Inoculation with Botulinum Toxin", Human Gene Therapy, vol. 13, No. 2, Jan. 20, 2002, pp. 225-232.

* cited by examiner

Figure 1

NEURONAL GENE TRANSFER OF ADENOVIRUS AND HERPES VIRUS VECTORS

This application is the US national phase of international application PCT/EP02/05354 filed 15 May 2002 which designated the U.S., the entire contents of which is incorporated herein by reference.

FIELD OF INVENTION

The present invention relates to the fields of genetics and medicine. More particularly, the invention relates to compositions and methods for the delivery of nucleic acids to neurons in a mammal, and uses thereof. The present invention specifically discloses the use of compounds that cause synaptic nerve sprouting to increase neuron retrograde transport of a vector or a product (a polypeptide or a nucleic acid for example) in a mammal. The invention is also based on the use of a compound that interacts with synaptosomal associated proteins to increase neuron retrograde transport of a vector or a product such as one cited above in a mammal. The invention also relates to a product comprising a viral vector comprising a transgene and a compound that causes synaptic nerve sprouting, for sequential use for delivering said transgene to neurons by retrograde transport and its uses for the preparation of a composition used as a treatment in several neurological disorders. The methods and compositions of this invention can be used to deliver various transgenes, such as markers, vaccines, therapeutic genes etc., and are suitable for experimental, therapeutic or various other applications.

BACKGROUND OF THE INVENTION

Transfer of information between two neurons or order cross from a neuron to a target cell, such as a motor neuron and a contractil muscular fiber, occurs through junctions named synapsis.

The main synaptic way of communication implies emission of chemical molecules or neurotransmitters from nerve terminals of the transmitter neuron (presynaptic neuron), which are taken up by the receiving postsynaptic cell. Acetylcholine intervenes as a neurotransmitter between motor neurons and streaked skeletal muscles for example.

In nerve terminals, chemical molecules are stocked into synaptic vesicles which are made of small and spherical organelles of 50 nm in diameter, delimited by a lipidic membrane. Those molecules are up to 500 000 in nerve terminals. To command a volountary impulse or movement or to keep a position, contraction order is given to muscles by way of several bioelectrical impulsions. Each impulsion spreads up to nerve terminals of motoneurons and depolarizes them. Synaptosomal associated proteins, namely ionic chanels, are activated and rendered permeable to calcium ions which get in the nerve terminals. This induces the fusion of synaptic vesicles with nerve terminal membranes. By this way, vesicles neurotransmitters content is released through the synaptic slot between transmitter neuron and target muscular fiber. This release is called exocytose. Acetylcholine diffuses through the synaptic slot and then molecules are detected by acetylcholine receptors localized on muscular fibers. This detection induces a postsynaptic signal, namely a depolarization, which creates an action potential.

Sometimes this mechanism of signal transduction is deficient. Amyotrophic lateral sclerosis is a devastating neurodegenerative disorder, affecting the motor neurons of the central nervous system (cortex, brainstem) and the peripheral motor neurons (spinal cord). The disease destroys the nerve cells that control voluntary movement and is characterized by progressive muscle weakening, paralysis and death, usually within 2 to 5 years after the appearance of the first clinical sign. The disease affects limbs, tongue, pharynx and larynx muscles. Onset usually occurs after age 45, and the rate and pattern of disease progression vary widely.

There is no treatment for this disease and its etiology remains unknown, although the discovery of missense mutations in the gene for copper-zinc superoxide dismutase (SOD1) in some pedigrees with familial ALS (FALS) has marked an important advance in the understanding of ALS physiopathology. Most ALS cases are sporadic (SALS), and of the 10% autosomal dominant inherited cases, about 20% of kindreds are associated with mutations in the SOD1 gene. Over 60 point mutations have been identified to date in all five exons of the SOD1 gene, involving 43 of the 153 residues.

The SOD1 enzyme plays a critical role in preventing cell damage by free radicals, by scavenging the superoxide anion radical, converting it into oxygen and hydrogen peroxide. Although the mechanism by which mutations in the gene encoding ubiquitous SOD1 protein lead to selective motor neuron degeneration is unknown, some such mutations cause motor neuron disease when expressed in transgenic mice. For example, G93A mutant mice (glycine to alanine substitution at position 93) develop progressive loss of motor neurons and vacuolar degeneration of mitochondria within motor neuron cell bodies of the spinal cord and the brainstem leading to a progressive decline in motor function and death at 5 to 6 months of age. Novel cytotoxic properties of the mutated SOD1, rather than a decrease in enzyme activity, are thought to be involved in this neurotoxicity. In particular, the SOD1 mutation may induce misaccumulation of the neurofilaments (NF), as has been described in both human and experimental ALS and a lower level of motor neuron degeneration combined with delayed progression of the disease has been reported in mice carrying both a SOD-1 mutation and a disrupted NF-L gene.

Others diseases such as spinal muscular atrophy (SMA), epilepsy, Parkinson's disease or Alzheimer's disease are also caused by neurological disorders. Furthermore, trauma associated with the spinal cord can induce neurological disorders.

A number of neurotrophic, neuroprotective and growth factors are potential candidates for treating ALS and other Motor Neuron Diseases (MND) (Alisky and Davidson, 2000). However, these factors delivered systemically have not been beneficial to patients in clinical trials. The reasons for this lack of success include limited access to motoneurons, insufficient specificity, or down-regulation of binding sites (Sendtner, 1997). Therapeutic gene transfer offers potential advantages over direct administration of the protein, such as continuous and/or targeted production of the desired transgene in vivo. The continuous in situ production of physiological concentrations of growth factors by gene transfer may allow the expression of the potential therapeutic effect of such molecules (Gravel et al., 1997; Alisky and Davidson, 2000). Retrograde axonal transport of recombinant adenoviral vectors has been used successfully to deliver genes to motoneurons in mammalians following injection of the vectors into muscles (cf: WO 98/31395). However, it seems that only a small proportion of motoneurons take up and retrogradely transport adenoviral particles.

Intramuscular injection of recombinant adenoviruses is an approach particularly well-suited to gene therapy of MND because it allows motoneuronal transduction and production of the therapeutic proteins in the Central Nervous System (CNS) after axonal retrograde transport of the vectors (Finiels et al., 1995; Ghadge et al., 1995). However, several recent studies reported that only a low percentage of motoneurons were transduced following peripheral administration of recombinant adenoviruses (Gravel et al., 1997; Perrelet et al., 2000). Intramuscular injection of recombinant adenoviruses into the facial musculature or into the tongue of mice resulted in less than 10% of motoneurons being transduced (Gravel et al., 1997). This could be due to only a subpopulation of spinal motoneurons being susceptible to infection (Perrelet et al., 2000). In agreement with these studies, a low rate of motoneuron transduction (4%) has also been observed in the mouse hypoglossal nucleus after injection of the Ad-RSV-βgal adenovirus into the tongue.

Direct intracerebral injection of adenoviral vectors into various brain structures allows the transfer of a therapeutic gene both at the injection site and also at distance, via neurons that send axonal projections to the injection site (Akli et al., 1993; Davidson et al., 1993; Le Gal La Salle et al., 1993). This observation suggests that adenoviral particles are taken up at nerve terminals and are retrogradely transported to the neuronal cell bodies. For example, neurons located in the substantia nigra or in the inferior olive can be efficiently transduced by inoculation of the striatum and the cerebellum, respectively, with the vectors (Akli et al., 1993; Ridoux et al., 1994). This remarkable property renders recombinant adenoviruses particularly useful for retrograde neuronal tracing in the CNS (Ridoux et al., 1994; Kuo et al., 1995). Another application of this property is for the transduction of the not easily accessible motoneurons by peripheral injection of the vectors (Finiels et al., 1995; Ghadge et al., 1995). This route of administration is particularly suitable for treating fatal neurodegenerative diseases affecting motoneurons (Alisky and Davidson, 2000). It is a preferable alternative to more invasive intramedullar injections with gene vectors. However, as indicated above, the percentage of motoneurons transduced is low, even when large doses of the vector are used (Gravel et al., 1997; Perrelet et al., 2000). Another potential problem is ectopic production of the exogenous protein, i.e., the presence of the protein in the muscle may result in side effects.

The invention now provides an improvement to gene delivery to motor neurons, particularly to the "retrograde transport approach" and allows an overexpression of any polypeptide or nucleic acid in said neurons in vivo. The invention stems from the use of various compounds that cause synaptic nerve sprouting, which significantly improve retrograde transport and gene expression into neurons. The invention also discloses improved vectors designed to specifically transduce the neurons when injected into the brain or muscles which further improve the efficacy, selectivity and safety of the proposed methods.

SUMMARY OF THE INVENTION

The invention relates to compositions and methods to allow efficient retrograde transport of gene vectors or any other product (a polypeptide or a nucleic acid for example) into neurons. The invention relates more specifically to the combined use of gene delivery vectors and particular compounds that cause synaptic nerve sprouting, to provide improved gene delivery in vivo.

The present invention indeed discloses a new pharmacological approach for increasing gene delivery to neurons upon intramuscular or intracerebral injection of recombinant viruses. This method is based on the injection of a compound that induces synaptic sprouting at the neuronal junction, preferably prior to that of the vector or of the product and at essentially the same location. The invention shows that pre-injection with a compound causing sprouting, results in a remarkable improvement of viral gene transfer to various groups of neurons. An object of this invention thus resides in the use of a product that causes synaptic nerve sprouting or that causes an increase of neuronal plasticity and endocytosis for the preparation of a composition to increase neuron retrograde transport of a vector in a mammal.

In addition, the present invention further shows that, surprisingly, compounds that cause nerve sprouting not only increase the number of transduced neurons, but also increase the expression level of a transgene in each neuron. Accordingly, such compounds are useful in the manufacture of a composition for the treatment of the human body. The present invention also relates, for instance to a product comprising a viral vector comprising a transgene and a compound that causes synaptic nerve sprouting, for sequential use for delivering said transgene to neurons by intramuscular or intracerebral injection and retrograde transport. In particular, compounds having the ability to increase synaptic nerve sprouting and neuron retrograde transport represent high potential compounds for the treatment of neuron diseases such as amyotrophic lateral sclerosis, epilepsy, Parkinson's disease or Alzheimer's disease for example. Targets or receptors of those compounds also represent an interesting target for the development of drugs or pharmacologically active composition which could then be used for pharmaceutical, therapeutical or experimental purposes.

LEGEND TO THE DRAWINGS

FIG. 1: Dose-response curve for BoNT pre-treatment and motoneuronal transduction. Luciferase activity in the brainstem (black) and in the tongue (white) 8 days after injection of Ad-N12-PGK-luc into the tongue of mice pretreated with PBS or BoNT (1.25 to 250 pg). Luciferase activity is expressed in rlu/μg of total protein. Data are means +/− SEM for 3 to 6 animals. A student's t-test was used to compare each BoNT-treated group to the PBS control group (*$p<0.05$; $p<0.01$; *$p<0.001$).

FIG. 2: β-galactosidase-expressing motoneurons in the hypoglossal nucleus after Ad-RSV-β-gal administration into tongues pre-injected with PBS (A,D), 12.5 pg of BoNT (B,E) or 25 pg of BoNT (C,F). (A,B,C) are at low magnification and the bar is 50 μm. (B,D,F) show details of hypoglossal motoneurons expressing β-galactosidase at high magnification (bar=25 μm). Note the strong β-galactosidase expression overflowing from the nucleus into the motoneuron cytoplasm and the neuritis in (E,F).

Figure 3:
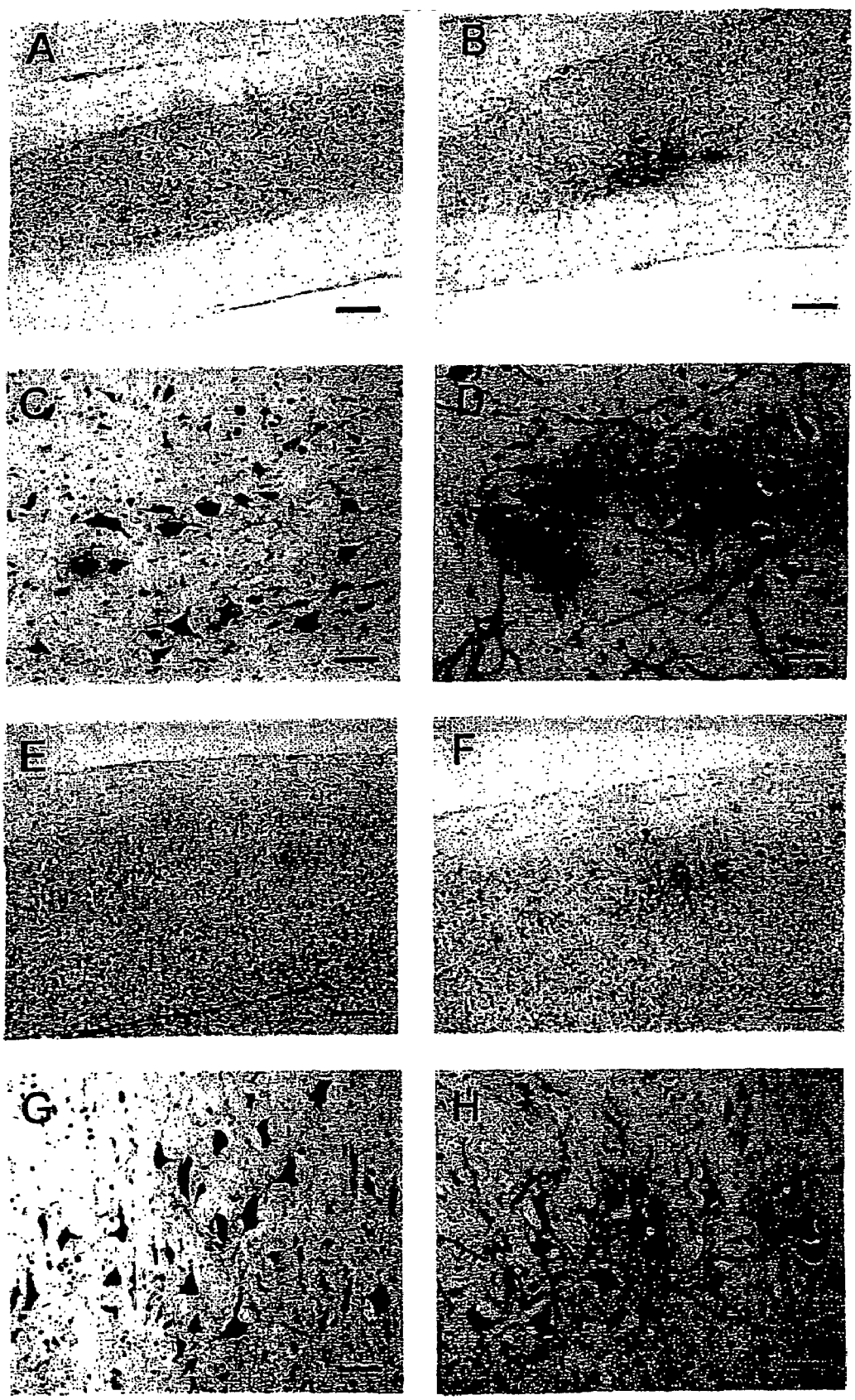

FIG. 3: β-galactosidase-expressing motoneurons in the cervical (A-D) and the lumbar cord (E-H) one week after injection of Ad-RSV-β-gal into the left tibialis and the right gastrocnemius muscles, respectively. Muscles were pre-injected with PBS (left panels) or 12.5 pg of BoNT (right panels). (A,B,E,F) low magnification, bar is 200 μm. (C,D, G,H) high power magnification, bar is 50 μm.

DETAILED DESCRIPTION OF THE INVENTION

This invention resides, generally, in the use of a compound that causes synaptic nerve sprouting for the preparation of a composition to increase neuron retrograde transport of a vector or a product such as a polypeptide or a nucleic acid, in a mammal and preferably in a human.

The vectors used in the present invention may be any viral or non viral vectors suitable for introducing nucleic acids into a cell in vivo. Non-viral vectors include plasmids which can be used together with liposomes, electrically charged lipids (cytofectins), DNA-protein complexes and biopolymers. In a preferred embodiment, the vectors are viral vectors, preferably adenoviruses, herpes viruses, adeno-associated viruses (AAV), retroviruses including lentiviruses, poxviridae, baculovirus, vaccinia or Epstein-Barr viruses. Most preferred vectors are adenoviruses.

Various serotypes of adenovirus exist. Of these serotypes, preference is given, within the scope of the present invention, to using type 2 or type 5 human adenoviruses (Ad 2 or Ad 5) or adenoviruses of animal origin such as adenoviruses of bovine, murine, ovine, porcine, avian and simian origin. A preferred animal adenovirus is canine such as CAV2 adenovirus. Studies have shown that adenovirus are capable of infecting with a very high efficiency cells of the CNS ((cf: WO 99/41396, FR 2 774 698 and WO 98/31395). Recombinant adenoviruses carrying a replication defective genome may be prepared according to methods known in the art using either competent packaging cells or transient transfection (Graham F. L. and Prevec L., Gene transfer and expression protocols; Manipulation of adenovirus vectors, Methods in Molecular Biology (1991), The Humana Press Inc, Cliften, N.J., chapter 11, pp.109-128). Preferred vectors are replication-defective adenoviruses, comprising at least one non-functional viral region selected from E1, E2 and/or E4. Such adenoviruses may be produced according to conventional methods, as described for instance in Dedieu et al., Journal of virology 71 (1997), pp. 4626-4637. In a particular embodiment, the adenovirus is a "minimum" vector or a "gutless" vector, i.e., comprises an adenoviral genome devoid of all functional viral genes. Such vectors may be produced as described for instance in Mitani et al., PNAS 92 (1995), pp. 3854-3858 and in Parks et al., PNAS 93 (1996), pp. 13565-13570.

Retroviral or AAV vectors may be produced following conventional techniques as described for instance in WO 92/07943, WO 90/02806, U.S. Pat. No. 5,278,056; WO 97/09441; WO 97/06272, WO 96/39530, WO 95/34671, WO 96/22378.

Most preferably, the vector provides a regulated expression of the transgene. For instance, although expression may be constitutive and/or ubiquitous, preferred vectors provide for tissue-specific or inducible gene expression. Tissue-specific expression can be achieved with regulated or tissue-specific promoters, such as NSE (neuron-specific enolase), etc. Alternatively, regulated expression may be obtained using silencer elements that control expression from ubiquitous promoters.

Typically, a neuron-restrictive silencer element (NRSE) may be used in front of a ubiquitous promoter in the vectors according to the present invention, thereby limiting transgene expression to the neurons and essentially avoiding expression in muscle cells. Examples of suitable, constitutive or tissue-specific promoters are described in WO 99/41396 and FR 2 774 698 and includes, for instance, viral promoters (RSV; LTR; CMV) or other promoters active in mammalian cells (actin, fibrin, PGK, enolase, etc.).

The transgene to be delivered to the neurons may be any DNA or RNA encoding a polypeptide or antisense of interest.

The polypeptide may be any marker or any biologically active molecule, such as a growth factor, a cytokine, a lymphokine, a neurotrophic factor, etc. Typical examples include NT-3, NT4, NT-5, CNTF, GDNF, interferon, TNF, IGF, interleukins, etc.

The invention is based on the use of compounds that induce or cause or stimulate nerve sprouting, particularly synaptic nerve sprouting (e.g., at a neuromuscular junction), and/or that cause or induce or stimulate neuronal plasticity or endocytosis. Indeed, the invention now surprisingly shows that, by altering the physiological state of terminal junction or nerve ends, it is possible to increase very significantly the retrograde transport of a vector into neurons. Various compounds may be used according to this invention such as botulinum toxins but also neurotrophic factors for example.

In a typical embodiment, botulinum neurotoxin and especially botulinum neurotoxin A (BoNT) is used to enhance gene transfer to motoneurons innervating the injected muscles. Modifications in motoneuron transduction is a consequence of toxin-induced nerve sprouting at the end-plates.

This invention stems notably from the unexpected discovery that pre-injection of type A BoNT into muscles greatly improves gene transfer into motoneurons by retrograde transport of recombinant adenoviruses.

Similarly, retrograde transport of adenoviral vectors may also be improved by the use of the other botulinum toxins and analogs thereof, as well as of neurotrophic factors, particularly Insulin-like growth factor 2 (IGF-2), ciliary neurotrophic factor (CNTF), neurotrophin-4 (NT-4), Neurotrophin-3 (NT-3) or GDNF for example.

The present invention includes the use of a compound that causes an increase of neuronal plasticity and endocytosis for the preparation of a composition to increase neuron retrograde transport of a vector in a mammal.

In an embodiment of the present invention, induction of this plasticity is consecutive to the blockade of the cholinergic transmission as a compensatory mechanism: BoNT cleaves SNAP-25 (synaptosomal associated protein of 25 kDa), a membrane protein of the synaptic vesicle (Schiavo et al., 1993), and the consequence is that acetylcholine release is blocked (Ambache, 1949, Burgen et al., 1949). Botulinum toxins arrest vesicle exocytosis without preventing endocytosis. Rather, the increase in motor neuron transduction observed in botulinum treated mammals demonstrates that vesicles endocytosis is increased by the toxin in vivo.

The invention thus includes the use of any compound that causes a cleavage of synaptosomal associated protein SNAP-25 or of any other proteins involved in vesicle exocytosis and synaptic nerve sprouting for the preparation of a composition to increase neuron retrograde transport of a vector or of a product such as a polypeptide or a nucleic acid.

In another embodiment of the invention, it has been demonstrated that the greater endocytosis observed after the use of a compound that causes an increase of neuronal plasticity and/or synaptic nerve sprouting, is due to activation of GAP-43, a growth-associated protein, present in growth cones and synaptic terminals and implicated in sprouting and endocytosis. GAP-43 is bound by calmoduline when $Ca^{2+}$ levels are low, and released when $Ca^{2+}$ levels rise. During activity-dependent increases in $Ca^{2+}$ levels, GAP-43 interacts with rabaptin-5, a protein involved in endocytosis. As GAP-43 is negatively regulated by the phosphatase activity of calcineurin, the phosphorylation state of GAP-43 increases secondarily to the calcineurin inhibition due to ALS, similarly to what is observed in cells overexpressing SOD-1 mutants.

The immunoreactivity of GAP-43 is high in both the spinal cord and nerve terminals of patients with ALS and in motor end plates and axons in botulinum-treated mammals.

The invention demonstrates the involvement of an alternative endocytosis. pathway regulated by GAP-43, in the increase in uptake observed both in ALS and in botulinum-treated mammals. Therefore the invention includes the use of any compound that activates GAP-43 for the preparation of a composition to increase neuron retrograde transport of a vector or any other product in a mammal.

The invention further relates to the use of a compound that causes synaptic nerve sprouting at a neuromuscular junction for the preparation of a composition to increase retrograde transport of a product or an adenoviral vector in motoneurons in a mammal.

This method of gene transfer is applicable in mammalian subjects, particularly humans, more particularly those suffering from degenerative disorders such as ALS, even after the onset of the first clinical signs of disease allowing diagnosis. According to the invention, retrograde gene transfer efficacy is improved by synaptic sprouting.

The improved product or virus gene transfer and especially adenovirus gene transfer, in the motor neurons of symptomatic ALS mammals, despite the misaccumulation of neurofilaments and abnormalities in axonal transport reported in these mammals, is a striking finding demonstrating the plasticity of ALS motor neurons, which compensate for the loss of nerve fibers by acquiring new capacities for viral particles uptake.

The invention discloses also another unexpected discovery, namely that BoNT and analogues thereof, not only induce an increase in the number of transduced neurons, but also result in stronger transgene expression within these neurons. Another embodiment of the present invention is a product comprising (i) a viral vector comprising a transgene and (ii) a compound that causes synaptic nerve sprouting, for sequential use for delivering said transgene to neurons by intramuscular or intracerebral injection and retrograde transport.

The compounds and vectors according to this invention may be administered preferably by intracerebral or intramuscular injection.

In the case of an intramuscular injection, administration may be performed into muscles of the upper limbs (biceps, triceps). This makes it possible to transfer a gene into the motor neurons at the cervical level. Administration into the muscles of the thorax (pectoral muscles) makes it possible to transfer a gene into the motor neurons at the thoracic level; administration into the muscles of the lower limbs (gastrocnemial muscles) makes it possible to transfer a gene into the motor neurons at the lumbar and sacral levels. Other muscles may of course be used for administration into these motor neurons, and other motor neurons may also be targeted.

The selected neurons can be any type of neurons. In a preferred embodiment those neurons are cholinergic or dopaminergic neurons for example.

Most preferably, the compound(s), product(s) and vector(s) are administered essentially at the same location or within the same tissue. Various protocols may be used for the administration, such as simultaneous or sequential administration, single or repeated administration, etc., which may be adjusted by the skilled person. Preferably, the compound causing nerve sprouting is administered prior to the vector, for instance between 5 hours to 2 weeks prior to the vector, typically between 1 day to 1 week prior to the vector. The doses of compound and vector may be adjusted by the skilled person depending on the route of administration, tissue, vector, compound, etc.

Typically, between about $10^4$-$10^{12}$ pfu of viral vector, preferably between about $10^5$-$10^{10}$ pfu, and even more preferably between about $5\times10^5$ and $5\times10^9$ pfu of virus is used.

The virus may be purified and injected as a suspension in any suitable composition or buffer, comprising pharmaceutically acceptable excipients or vehicle (PBS, salts, isotonic solution, stabilizing agents, etc.).

The compounds may be injected at various doses, selected and/or adjusted by the skilled person. Selection comprises determination of dose effective to produce sprouting without essentially causing toxicity. As an example, botulinum toxins may be injected at doses varying between about 1-500 pg, preferably between 10-300 pg, more preferably between 10-150 pg, even more preferably between 10-100 pg.

Neurotrophic factors may be injected at doses varying between 1-1000 μg, for instance. The compounds are preferably formulated in liquid suspension, with isotonic solutions or excipients, as described above.

The injection of retrogradely transported gene vectors is a valuable therapeutic approach in various neurological diseases such as epilepsy, amyotrophic lateral sclerosis, Parkinson's disease and Alzheimer's disease and also in muscular accidents involving a neuron injury. Gene delivery according to this invention may also be used for experimental research, clinical research, diagnostic or other purposes (animal studies, etc.).

Further advantages and aspects of this invention will be disclosed in the following examples, which should be regarded as illustrative and not limiting the scope of the present application.

EXAMPLES

1. Materials and Methods

1.1 Recombinant Adenoviruses

Ad-N12PGK-luc contains 12 NRSE sequences in front of the mouse phosphoglycerate kinase (PGK) promoter to target expression of the luciferase enzyme to neurons. Ad-RSV-βgal contains the Rous sarcoma virus long terminal repeat (RSV LTR) promoter and encodes a β-galactosidase targeted to the nucleus by the SV40 nuclear localization signal (Strafford-Perricaudet et al., 1992). These first generation recombinant adenoviruses were generated by homologous recombination (Strafford-Perricaudet et al., 1992). Viral stocks were prepared in 293 cells using standard amplification procedures. Virus titers were measured by optical density and checked using the plaque assay method. Both viral stocks had a titer of $1.10^8$ plaque-forming units (pfu).$\mu l^{-1}$.

1.2 Animals and Injection Procedures

C57BL6 mice were provided by Charles River (France). All animals were maintained and treated according to the guidelines of the European Community. Before intramuscular injections, mice were deeply anesthetized with Rompun (Bayer)/Ketamine (UVA). Doses from 1.25 to 250 pg of type A BoNT (Sigma) were diluted in 10 μl of phosphate-buffered saline (PBS) and injected into 4 sites in the tongue of mice at a rate of 2.5 $\mu l.mn^{-1}$. Control animals were injected with PBS. Following injections, mice received standard food pellet bruised in water ad libitum. One week after BoNT or PBS treatment, mice were injected with $10^9$ pfu of Ad-N12PGK-luc or Ad-RSV-βgal diluted in PBS as described above. Injections into the tibialis and the gastrocnemius were given by a similar procedure: 10 μl of PBS containing 12.5 pg of BoNT was administered to two sites in the muscle.

1.3 Measurement of Luciferase Activity

Mice were killed by overdose of pentobarbital (Sanofi) 8 days after adenoviral injection. Brainstems and tongues were removed, dissociated in lysis buffer and luciferase activity was assessed using a LUMAT LB9501 luminometer (Berthold) as previously described (Millecamps et al., 1999). Luciferase values are normalized according to the amount of protein in cell extracts determined by the Bio-Rad assay (Bio-Rad Laboratories).

1.4 Detection of β-galactosidase Activity

One week after intralingual injections of Ad-RSV-βgal, mice were anesthetized with pentobarbital and perfused with PBS containing 4% paraformaldehyde (PFA). Brains and spinal cords were removed, postfixed for 2 hours in the PFA solution, cryoprotected in 30% sucrose overnight, embedded in Tissue Tek and frozen by immersion in isopentane at −40° C. Transversal brain and longitudinal spinal cord sections (16 μm) were cut with a cryostat and incubated for 12 hours in PBS containing the 5-bromo-4-chloro-3-indoyl-β-D-galactosidase substrate (X-Gal, 0.4 mg/ml, Appligene) with 4 mM potassium ferricyanide (Sigma), 4 mM potassium ferrocyanide (Merck) and 2 mM $MgCl_2$ (Merck) for detection of β-galactosidase activity. Sections were then rinsed in PBS, counterstained with neutral red and mounted.

1.5 Cell Counting

X-Gal-positive motoneurons were counted on every fourth section of the hypoglossal nucleus and of the ventral spinal cord. Neutral red-stained motoneurons in the hypoglossal nucleus were counted on every fourth section of the brainstem. Raw values were corrected according to Abercrombie's formula (Abercrombie, 1946).

2. Results 2.1 BoNT Increases Brainstem Luciferase Expression after Intralingual Injection of an Adenoviral Vector Encoding Luciferase To test whether BoNT could increase gene transfer into motoneurons, various concentrations of BoNT were injected into muscles one week before intramuscular adenovirus inoculation. The efficacy of retrograde axonal transport to the motoneuron soma was investigated by measuring luciferase expression in the brainstem of the BoNT-treated mice. To restrict the expression of the luciferase gene to motoneurons, the NRSE-PGK combined promoter (Ad-N12PGK-luc) was used. A two factor analysis of variance (ANOVA) was used to analyze the differences in luciferase activity according to the dose of BoNT and the site of expression. The interaction between the two factors was significant ($p=0.0001$) indicating that the effect of BoNT treatment on luciferase expression differed between the tongue and the brainstem. A Student's t-test was used for intergroup (BoNT/PBS) comparison of luciferase activity in the brainstem and in the tongue. In the brainstem, luciferase activity was significantly higher in mice treated with doses of BoNT of between 12.5 pg and 250 pg (the highest dose that we tested) than in PBS-treated mice (FIG. 1).

It increased surprisingly with the dose of BoNT (to 10 fold at 12.5 pg), to a maximum at 25 pg (to 30 fold). At BoNT doses above 125 pg luciferase expression was lower. In contrast, luciferase activity in the tongue was the same for all concentrations of BoNT and in all groups (FIG. 1).

Whether the increase in motoneuronal gene transfer was due to the BoNT induced-sprouting or to the presence of the toxin in the tongue was further investigated. Simultaneous injection with 25 pg of BoNT and $10^9$ pfu of Ad-N12PGK-luc did not modify the level of transgene expression in the brainstem. Luciferase activity in BoNT/Ad-N12-PGK-luc-treated mouse was similar to that in PBS-treated animals (1.97 rlu/μg protein vs 3.04+/−0.9 rlu/μg protein for PBS treated group) and much lower than that in mice treated with the toxin 8 days before adenoviral inoculation (93.05+/−3.62 rlu/μg protein). The BoNT-induced increase in motoneuronal gene expression is therefore not a consequence of the presence of BoNT, but is due to the synaptic sprouting caused by the toxin.

2.2 BoNT Increases the Number of Transduced Motoneurons in the Hypoglossal Nucleus After Intralingual Injection of an Adenovirus Encoding β-galactosidase To analyze the effect of BoNT pre-injection on the number of transduced motoneurons in the brainstem, 12.5 or 25 pg of BoNT was injected into the tongue 8 days before inoculation with an adenovirus expressing a nuclear-targeted β-galactosidase under the control of the RSV promoter. One week following adenovirus injection, strong β-galactosidase expression was observed in the hypoglossal motoneurons of animals treated with BoNT (FIG. 2). The number of transduced motoneurons was significantly higher in the hypoglossal nucleus of mice treated with 25 pg BoNT (10 fold), than in that of control mice treated with PBS ($p=0.0001$) (Table).

Section of the hypoglossal nuclei of these animals were stained with neutral red and motoneurons were counted. BoNT-(2351.3+/−50.1) and PBS-treated (2332.8+/−59.7) groups had similar numbers of motoneurons indicating that treatment with 25 pg of BoNT was not toxic for these cells. The number of transduced cells per 100 motoneurons in the hypoglossal nucleus was therefore markedly higher in mice treated with 25 pg of BoNT (40%) than in those treated with PBS (4%).

In addition, the level of transgene expression in transduced motoneurons was higher in BoNT-treated animals: β-galactosidase expression was so strong that is was not only detected in the nucleus of the transduced motoneurons but also in the cytoplasm and in the axons forming the root of the hypoglossal nerve (FIG. 2).

2.3 BoNT Pretreatment Increases Gene Transfer to Motoneurons Following Adenoviral Injection in Diverse Muscle Groups Whether BoNT-pretreatment promoted motoneuron transduction in other muscle groups was tested. Mice were injected in the left tibialis and the right gastrocnemius muscles with either 12.5 pg of BoNT or with PBS one week before Ad-RSV-βgal inoculation. Expression of β-galactosidase was assessed in the spinal cord at the cervical and the lumbar levels, respectively. Strong expression of β-galactosidase was observed in both cervical and lumbar motoneurons in all animals pretreated with BoNT. As in the hypoglossal nucleus, X-gal staining was also detected outside the nucleus, in the soma and the neurites (FIG. 3). All transduced cells were located in the ventral cord ipsilateral to the injection site. The mean number of transduced motoneurons was up to 3.2 times higher in the lumbar cord and up to 2.5 times higher in the cervical cord of BoNT-treated than PBS-treated animals, following injection into the tibialis and the gastrocnemius muscles, respectively.

|  | PBS injected | 12.5 pg | 25 pg |
|---|---|---|---|
| Hypoglossal nucleus | 101.97 +/− 7.39 (n = 4) | 226 (n = 1) | 981.85 +/− 89.88 (n = 4) |
| Cervical cord | 48.48 +/− 18.15 (n = 2) | 155.67 +/− 19.76 (n = 3) | ND |
| Lumbar cord | 22.7 +/− 7.73 (n = 3) | 55.39 +/− 14.46 (n = 3) | ND |

Injection of BoNT into the tongue prior to Ad-N12-PGK-luc inoculation at the same injection site resulted in a large increase in brainstem luciferase activity. Transgene expression measured in the brainstem was higher than that in the tongue if more than 12.5 pg of BoNT had been injected before administration of an adenoviral vector designed specifically to express transgenes in neurons. A significant increase in motoneuron transduction was obtained with BoNT doses of 12.5 and 25 pg (10 and 30 fold increase respectively). Increasing BoNT concentrations did not further improve the level of motoneuron transduction. Indeed, a slightly lower luciferase expression was even observed with doses above 25 pg of BoNT probably because of the systemic toxicity of high doses of the toxin (250 pg corresponds to double the mouse $LD_{50}$ as measured by intraperitoneal injection).

Similarly, injection of 25 pg of BoNT before intralingual inoculation with Ad-RSV-βgal resulted in a 10 fold increase in motoneuron transduction. The invention indicate that BoNT not only induces increase in the number of transduced motoneurons, but also results in stronger transgene expression within these motoneurons. Overall, there was a 30 fold-increase in luciferase expression after injection of Ad-N12PGK-luc due to treatment with 25 pg BoNT. This appears to be made up of a 10-fold increase in the rate of transduction and a 3 fold-increase in transgene expression in each transduced motoneuron. Those findings using β-galactosidase as the marker after BoNT treatment, are consistent with those for luciferase.

The BoNT-induced increase in gene transfer was not dependent on the simultaneous presence of the toxin and the vector, as no increase in motoneuronal gene transfer was observed when virus and toxin were administered together. BoNT induces sprouting at the end-plates beginning at 6 days after injection of the toxin into the tongue (Watson, 1969). This invention shows that BoNT or neurotrophic factors improves retrograde gene transfer by stimulating synaptic sprouting at neuromuscular end-plates.

In conclusion, this invention demonstrates notably that intramuscular pre-injection of BoNT greatly increases gene transfer to motoneurons by intramuscular injection of adenoviral vectors. This method is particularly relevant to situation in which retrograde axonal transport of gene vectors is the only way to provide a significant number of motoneurons with the therapeutic factor. In contrast to vectors expressing secretable and diffusible proteins (like growth factors), vectors expressing non-secretable proteins (like antiapoptotic, antioxidative, or calcium-buffering proteins) may have to be injected into many sites along the medullar parenchyma to transduce a significant number of motoneurons. The invasive aspect, and the risk of infection associated with multi-site injections into the spinal cord limit the clinical applications of this method. Retrograde axonal transport of viral gene vectors overcomes these problems: much less invasive intramuscular injections allow the production of the therapeutic proteins within motoneurons. Increasing the efficacy of this method of gene delivery by the use of agents, like the BoNT for example, that stimulate the nerve sprouting process is of great therapeutic value for ALS and other MND. This strategy can be used clinically as this toxin is already successfully used as a painless treatment for several neurological disorders (Bentioglio and Albanese, 1999; Naumann et al., 1999) and for various dermatological purposes (Odderson, 1998; Carruthers and Carruthers, 1998).

The invention claimed is:

1. A method for increasing in a mammal neuron retrograde transport of a viral nucleic acid vector selected from an adenovirus vector or herpes virus vector, the method comprising administering to the mammal said viral vector and a botulinum toxin that causes synaptic nerve sprouting said botulinium toxin being administered between one day to two weeks prior to the viral vector and essentially at the same location or within the same tissue as the viral vector.

2. The method of claim 1, to increase retrograde transport of the viral vector in motoneurons.

3. The method of claim 1, to increase retrograde transport of the viral vector in cholinergic or dopaminergic neurons.

4. The method of claim 1, wherein the botulinum toxin and the viral vector are administered by intracerebral injection.

5. The method of claim 1, wherein the botulinum toxin and the viral vector are administered by intramuscular injection.

6. The method of claim 1, wherein the mammal has a neurological disorder selected from the group of amyotrophic lateral sclerosis, epilepsy, Parkinson's disease, Alzheimer's disease, muscular accidents and trauma.

7. A method for increasing, in a mammal having a neurological disorder, neuron retrograde transport of a viral vector, selected from an adenovirus vector or herpes virus vector encoding a biologically active molecule, the method comprising administering to the mammal said vector by intracerebral or intramuscular injection and, one day to two weeks prior to said injection, administering to the mammal a botulinum toxin that causes synaptic nerve sprouting essentially at the same location or within the same tissue as the viral vector, wherein the administration of said botulinum toxin increases neuron retrograde transport of said adenoviral vector.

8. A product comprising (i) an adenovirus vector or a herpes virus vector comprising a transgene and (ii) a botulinum toxin that causes synaptic nerve sprouting, for sequential use for delivering said transgene to neurons by intramuscular or intracerebral injection and retrograde transport.

9. The method according to claim 1, wherein the botulinum toxin is botulinum neurotoxin A.

10. The method according to claim 7, wherein the botulinum toxin is botulinum neurotoxin A.

11. The product according to claim 8, wherein the botulinum toxin is botulinum neurotoxin A.

12. The method according to claim 7, wherein the biologically active molecule is selected from a growth factor, a cytokine, a lymphokine and a neurotrophic factor.

13. The product according to claim 8, wherein the transgene encodes a biologically active molecule selected from a growth factor, a cytokine, a lymphokine and a neurotrophic factor.

* * * * *